United States Patent [19]

Kelbrick et al.

[11] Patent Number: 5,534,222

[45] Date of Patent: Jul. 9, 1996

[54] METHOD FOR STERILIZING INTERNAL SURFACES OF AN EDIBLE LIQUID PACKAGING MACHINE

[75] Inventors: William J. Kelbrick; Vincent J. Rouble, both of Peterborough; Ralph D. Larmer, Fraserville; Stuart L. Pepper; Eric T. Warburton, both of Peterborough, all of Canada

[73] Assignee: Purity Packaging A Division of Great Pacific Enterprises, Peterborough, Canada

[21] Appl. No.: 503,897

[22] Filed: Jul. 11, 1995

[51] Int. Cl.[6] .............................. A61L 2/20; A61L 2/04
[52] U.S. Cl. .............................. 422/33; 422/28; 53/425; 53/426
[58] Field of Search .................... 422/1, 28, 33, 422/304; 53/425, 426, 440

[56] References Cited

U.S. PATENT DOCUMENTS

| | | | |
|---|---|---|---|
| 3,820,300 | 6/1974 | Reinecke et al. | 422/28 |
| 4,734,268 | 3/1988 | Redding et al. | 422/28 |
| 4,989,392 | 2/1991 | Lindgren et al. | 53/426 |
| 4,992,247 | 2/1991 | Foti | 422/31 |

*Primary Examiner*—Robert Warden
*Assistant Examiner*—Theresa T. Snider
*Attorney, Agent, or Firm*—Ridout & Maybee

[57] ABSTRACT

A method for the sterilization of the internal cabinet of a packaging machine, such as an edible liquid packaging machine, utilizes the introduction of a fog of hydrogen peroxide laden air into the cabinet of the machine followed by hot air. In particular, the method may be used to sterilize a machine that has an endless conveyor for receiving containers and transporting the containers to a container sterilization station, a product filling station, and a container sealing station all within the cabinet. The machine is equipped with a positive pressure airflow though it, whereby the air is passed through a plurality of HEPA (High Efficiency Particulate Absolute) filters prior to its entry into the machine cabinet.

7 Claims, 4 Drawing Sheets

METHOD FOR STERILIZING INTERNAL SURFACES OF AN EDIBLE LIQUID PACKAGING MACHINE

FIELD OF THE INVENTION

The invention is a method for sterilizing internal surfaces of a cabinet of a packaging machine such as an edible liquid packaging machine. The invention provides the means for packaging perishable goods, particularly an edible liquid such as milk or cream, under aseptic conditions.

The invention has particular utility in association with the packaging of milk or cream in small cups for use with coffee or tea. Large quantities of these milk or cream cups are used by the food service industry, which in turn require dairies to have packaging machines capable of meeting the huge demand. High speed liquid packaging machines have been developed to provide the necessary production capability for these milk or cream cups so that production can proceed at a rate of up to 2100 cups per minute. While prior versions of such packaging machines included a means for sterilizing the cups just prior to filling, the desirability of performing the entire packaging procedure under aseptic conditions has long been recognized.

BACKGROUND OF THE INVENTION

An edible liquid packaging machine has a variety of internal components which provide a myriad of small surfaces on which microorganisms may reside. It has been found that spraying the internal components of the machine cabinet with a disinfectant liquid is not effective in killing all microorganisms probably because the liquid does not reach all surfaces upon which microorganisms reside. A liquid spraying arrangement for such a machine must be operable when the machine is closed to the outside environment, and any such arrangement would require the provision of a plurality of spray nozzles, associated tubing and control systems to the packaging machine. This added complexity plus the doubtful effectiveness of such a system itself has resulted in the use of packaging machines of this type under less than ideal conditions. The present invention has solved the problem of providing an aseptic internal environment for an edible liquid packaging machine, thereby satisfying a long felt need in this art.

SUMMARY OF THE INVENTION

While the skilled person will appreciate that the invention has general applicability, the invention was developed particularly for the sterilization of the internal cabinet of an edible liquid packaging machine. Such a machine has an endless conveyor for receiving containers and transporting the containers to a container sterilization station, a product filling station, and a container sealing station all within the cabinet. The machine is equipped with a positive pressure airflow though it, whereby the air is passed through a plurality of HEPA (High Efficiency Particulate Absolute) filters prior to its entry into the machine cabinet. Means are also provided for heating an inflowing stream of air. The method of the invention comprises the steps of:

(1) maintaining the cabinet at an air temperature of 28°–32° C., and injecting a fine spray of aqueous hydrogen peroxide into air flowing into the cabinet, whereby the inflowing air is heated to 40°–48° C., and directing the inflowing hydrogen peroxide laden air sequentially into the container sterilizing station, the container sealing station, and the container filling station, so that a fog of condensed aqueous hydrogen peroxide is provided in the stations for sufficient periods to effect complete contact of all exposed surfaces with a bactericidal concentration of hydrogen peroxide; and (2) completing sterilization by heating the inflowing air so that the internal cabinet temperature is raised to 41°–47° C. and the temperature of the HEPA filters is raised to 36°–40° C., and maintaining the temperatures and air flows for a sufficient time to effect sterilization and drying of all exposed surfaces of the container sterilizing, filling and sealing stations.

DETAILED DESCRIPTION OF THE PREFERRED EMBODIMENT

Figure 1:
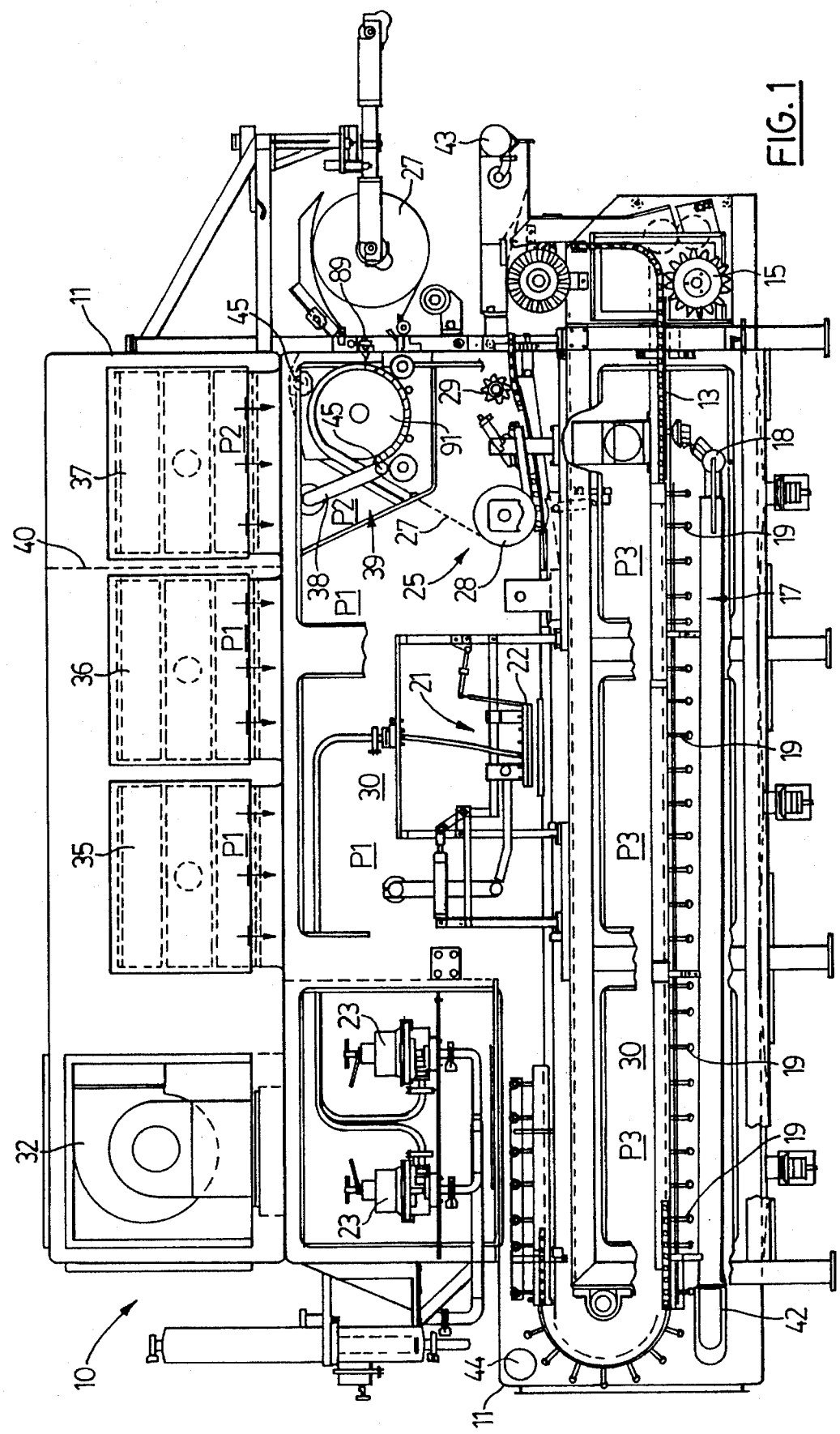
FIG. 1 is a front elevation of a packaging machine of the type in which the method of the invention is used.

As shown in FIG. 1, an edible liquid packaging machine 10 has a cabinet 11 containing an endless conveyor 13 which receives containers (not shown) from a fingered feed wheel 15. The containers fed onto the conveyor 13 move immediately to a container sterilization station 17 where they are first sprayed with aqueous hydrogen peroxide (preferably 33% $H_2O_2$) by means of a spray nozzle 18, followed immediately by exposure of the sprayed containers to a series of hot air nozzles 19 which quickly bring the temperature of the containers up to at least 100° C. The high temperature and hydrogen peroxide provide rapid and thorough sterilization of the containers during their few seconds of residence in this part of the machine 10.

The conveyor 13 transports the containers to a product filling station 21 where the cups are filled with the edible liquid by means of a multiple nozzle filling assembly 22. The filling station 21 is partitioned from pumps 23, so that the pumps 23 and related product delivery components are located outside the production area. The containers then immediately proceed to a sealing station 25 where rollform lidstock 27 is applied using a heated roller 28. The lidstock 27 is severed at a rotary knife 29, and the individual filled and sealed containers are ejected from the machine 10.

The shelf life of a perishable edible liquid depends directly on the sterility of the liquid and its container. Clearly, the shelf life of an edible liquid would be increased if a sterile liquid could be packaged under sterile conditions into a sterile container. The method of the invention provides an aseptic zone 30 for the cabinet 11 which includes the container sterilization station 17, the product filling station 21, and the container sealing station 25, thereby enabling the production of a packaged edible liquid having a longer shelf life than was heretofore possible.

Figure 2:
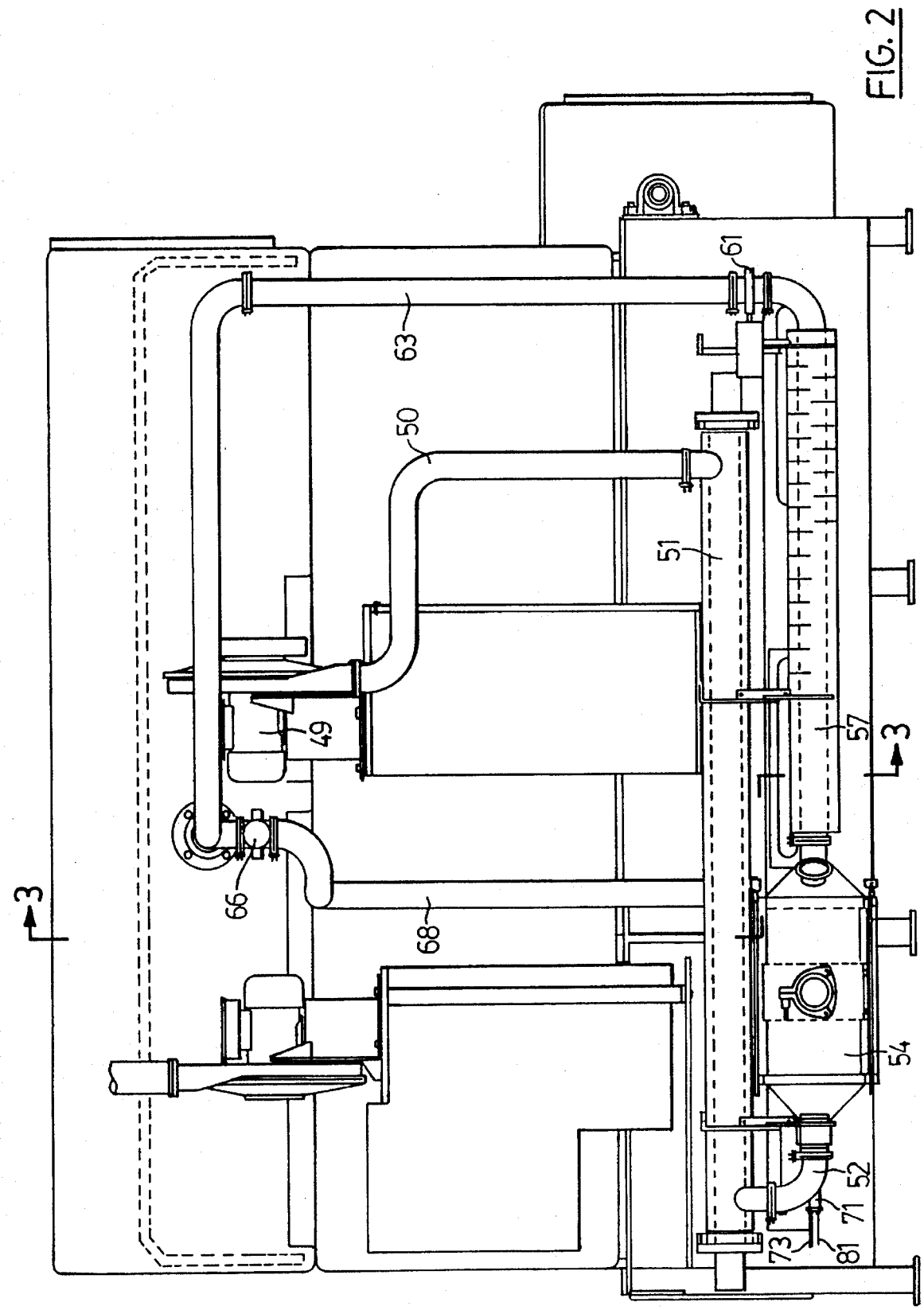
FIG. 2 is a rear elevation of the machine of FIG. 1 showing particulars of the air flow system for the machine.
Figure 3:
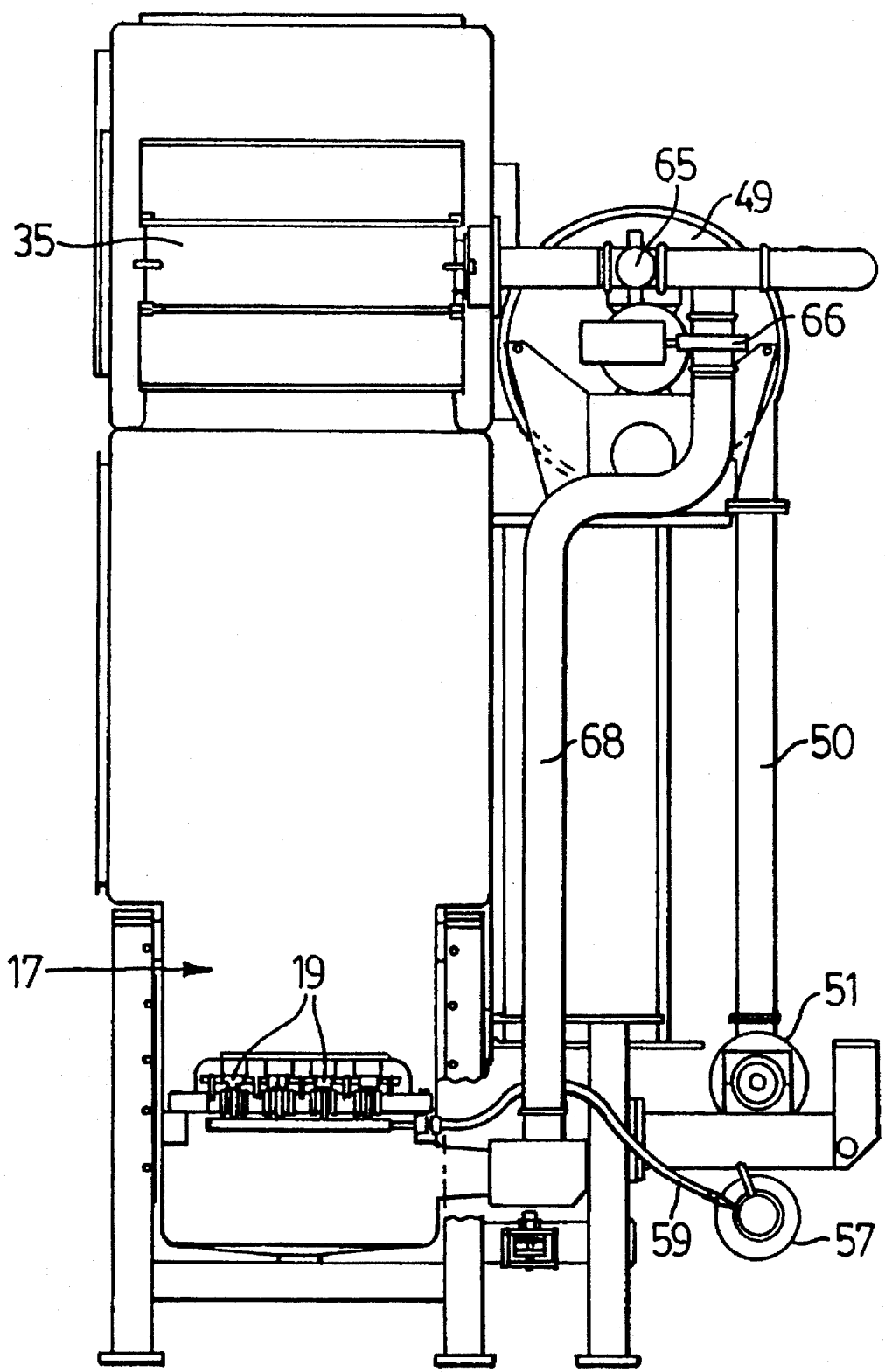
FIG. 3 is a cross sectional view taken along station 3—3 of FIG. 2.

As shown in FIGS. 1–3, the packaging machine 10 has an air flow system which introduces filtered aseptic air into the cabinet 11 and maintains a positive air pressure relative to atmospheric pressure in the aseptic zone 30 of the machine 10. This positive air pressure is provided principally by a blower 32 located in the top portion of the machine 10. The blower 32 provides a flow of air into the three dual HEPA filter assemblies 35–37 spaced along the top of the machine 10. The HEPA filters are preferably made of a nonwoven glass paper having a minimum 99.97%, 0.3 micron efficiency. A laminar air flow is provided by the air passing through the HEPA filter assemblies 35–37, so that positive air pressure zones can be applied to the aseptic areas of the machine 10. Thus, the product filling and container sealing stations 21 and 25 are at a pressure P1, and the container sterilizing station 17 is at a pressure P3. An internal portion of the lidstock feed assembly 38 is partitioned from the container sealing station 25 and provided with its own air supply from the HEPA filter assembly 37 directly above it. This arrangement provides a lidstock sterilizing zone 39 for the rollform lidstock 27 prior to its entry into the container sealing station 25. The HEPA filter assembly 37 is divided from the assemblies 35 and 36 by a baffle divider 40, thereby providing the filter assembly 37 and lidstock feed assembly 38 with a pressure P2. While means are provided in the lidstock sterilizing zone 39 to sterilize incoming lidstock 27 and to maintain aseptic conditions in the zone 39, this portion of the machine 10 is subject to a higher likelihood of microorganism contamination due to its proximity to the external environment. Thus, it is preferable to maintain a pressure P2 in the zone 39 which is less than the pressure P1 of the aseptic sealing station 25. The various pressures within the machine cabinet 11 preferably have the relationship to one another as P1>P2>P3>PA, where PA is the ambient atmospheric pressure.

Exhaust ducts are provided throughout the machine 10 to receive the flow of air coming into the cabinet 11 and to maintain the desired internal pressures. A main cabinet exhaust duct 42 is provided along the bottom of the container sterilizing station 17, with various other exhaust ducts being positioned about the cabinet 11. A front exhaust duct 43 provides air flow through the container sealing station 25, a rear exhaust duct 44 is located at the turn of the endless conveyor 13 leading into the filling station 21, and exhaust ducts 45 are located in the lidstock sterilizing zone 39.

The machine 10 also has a hot air supply system, the particulars of which are shown in FIGS. 2 and 3. A blower 49 directs air from the atmosphere through a conduit 50, into a heat exchanger 51 and then through an elbow 52 to a dual HEPA filter assembly 54. The heat exchanger 51 is preferably of the electrical type capable of heating the air stream to at least 165° C. as measured at the exit of the heat exchanger 51. From the HEPA filter assembly 54, the hot air passes into a hot air manifold 57 which is equipped with a plurality of take-off lines 59 supplying hot air to the nozzles 19 (FIG. 3). A valve 61 is located at the end of the hot air manifold 57, so that when the valve 61 is closed, all the hot air from the manifold 57 flows through the nozzles 19. When the valve 61 is open, the major portion of hot air flows through the conduit 63 to a junction point near the top of the machine 10 at which is located valves 65 and 66. With valve 65 open and valve 66 closed, the hot air flows into the upper HEPA filter assemblies 35–37, and with valve 65 closed and valve 66 open, the hot air flows down the conduit 68 and into the container sterilizing station 17.

The method of the invention requires the introduction of a bactericidal concentration of hydrogen peroxide into the cabinet 11 so that all microorganisms including mold and fungi spores on all exposed surfaces in the aseptic zone 30 and the lidstock sterilizing zone 39 are killed. Sterilization is effected by the combined action of hydrogen peroxide and heat. Prior attempts to sterilize the interior of the cabinet 11 using sprays of hydrogen peroxide within the cabinet 11 itself proved unsuccessful because it was not possible to achieve complete contact between the liquid spray and the myriad exposed surfaces. Additionally, drying the interior of the cabinet 11 after spraying was difficult and inefficient due to the tendency for the spraying step to create puddles of liquid within the cabinet 11. The present invention solves these problems by providing an atomized spray of aqueous hydrogen peroxide at the elbow 52 where the hot air exits the heat exchanger 51 so that a fog of hydrogen peroxide is introduced into the cabinet 11. The fog causes hydrogen peroxide to condense on all exposed surfaces within the cabinet 11 to effect sterilization while using far less hydrogen peroxide than was the case in prior ineffective procedures.

Figure 4:
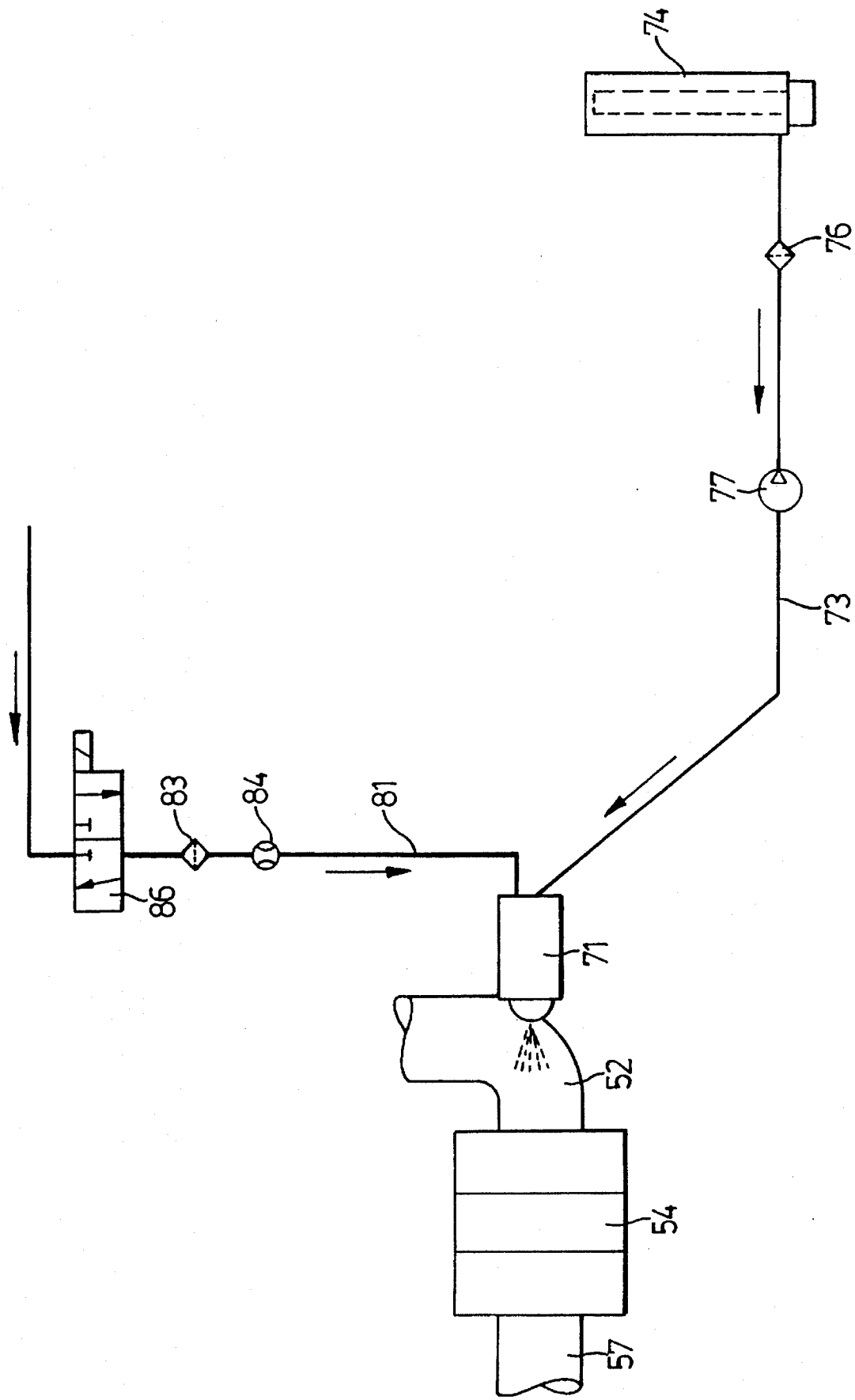
FIG. 4 is a schematic diagram of the hydrogen peroxide injection system for the machine.

As seen in the schematic of FIG. 4, a spray nozzle 71 is attached to and extends into the elbow 52. The nozzle 71 is supplied with aqueous hydrogen peroxide (preferably 33%) through a conduit 73 extending from a reservoir 74. The conduit 73 preferably has a filter 76, and the liquid is supplied to the nozzle 71 by a pump 77, such as a peristaltic pump. Aseptic air from the cabinet 11 is provided to the spray nozzle 71 through a conduit 81 which is preferably equipped with an in-line filter 83 and a flow meter 84. The conduit 81 is opened and closed by a solenoid valve 86.

In accordance with the invention, a spray of aqueous hydrogen peroxide is introduced into the elbow 52 through the nozzle 71 when the air temperature in the elbow 52 is about 40°–48° C. The air stream containing the fine spray of hydrogen peroxide proceeds immediately through the dual HEPA filter assembly 54 where all droplets are reduced to at least the pore size of the filter, i.e., 0.3 micron. The hydrogen peroxide laden air then moves into the hot air manifold 57 where it proceeds into the cabinet 11 through the nozzles 19 and possibly other conduits as dictated by the setting of the valves 61, 65 and 66. This hydrogen peroxide injection procedure creates a fog within the cabinet 11 in the following fashion. At the operating temperature of 40°–48° C. for the manifold 57, the hydrogen peroxide is essentially in the vapor phase. Upon the introduction of this hydrogen peroxide laden air into the cabinet 11 where the temperature is approximately 28°–32° C., a fog is created which causes a thorough wetting by condensation of all exposed surfaces within the cabinet 11. Because a fog of hydrogen peroxide is employed within the cabinet 11 rather than a spray of liquid, the formation of puddles is avoided. By following the fogging of the interior of the cabinet 11 with the application of hot air to bring the cabinet temperature up to about 41°–47° C., a complete sterilization and drying of the cabinet 11 is achieved.

A preferred cabinet sterilization procedure for the machine 10 will now be described. After physically cleaning the interior of the cabinet 11, the cabinet doors are closed and the cabinet 11 is brought up to the desired temperature of about 30° C. by introducing heated air from the manifold 57 into the container sterilizing station 17 using the blower 49. During the cabinet sterilization procedure, the main blower 32 is off and isolated from the cabinet 11 by a valve (not shown). The manifold temperature is about 44° C. for this cabinet heating and the subsequent steps involving the injection of hydrogen peroxide into the cabinet 11. Preferably, the hot air from the manifold 57 is directed through the nozzles 19 and the conduit 68 by opening the valves 61 and 66 while closing the valve 65. This cabinet warming step takes less than 5 min.

With all the valves 61, 65 and 66 closed, the conveyor 13 is engaged at a slow speed, and the introduction of hydrogen peroxide into the cabinet 11 is begun. In order to expose all surfaces of the conveyor 13 to hydrogen peroxide, the conveyor 13 moves at low speed throughout the sterilization procedure. An atomized spray of at least 33% aqueous hydrogen peroxide is introduced into the elbow 52 by means of the spray nozzle 71. As the valve 61 is closed, the hydrogen peroxide laden hot air in the manifold 57 proceeds through the plurality of nozzles 19 to introduce a fog of hydrogen peroxide into the container sterilizing station 17. In this manner 200 ml of aqueous hydrogen peroxide is introduced into the station 17 over about a 20 min. period. Simultaneously, the container spray nozzles 18 are activated to provide a spray of liquid droplets of aqueous hydrogen peroxide into the container sterilizing station 17. In this fashion, 60 ml of at least 33% hydrogen peroxide is introduced into the station 17 over 20 min. During this step, the temperature of the manifold 57 is about 44° C. and that of the cabinet 11 is about 31° C.

In the next step of the procedure, the valves 61 and 65 are opened to allow hydrogen peroxide laden air from the manifold 57 to flow into the HEPA filter assemblies 35–37 as well as to a lesser degree through the nozzles 19. The spray through the nozzle 18 is discontinued for this step, but a spray of liquid droplets of at least 33% aqueous hydrogen peroxide is introduced into the lidstock sterilizing zone 39 through a nozzle 89. The spray from the nozzle 89 is directed onto a sterilizing heater wheel 91 which during production rotates in contact with incoming lidstock 27 to sterilize it. During this step of the cabinet sterilization procedure, the heater wheel 91 is rotated and its temperature is maintained at about 136° C. Thus, the spray of aqueous hydrogen peroxide onto the wheel 91 is instantly vaporized, thereby producing an additional quantity of hydrogen peroxide fog for the lidstock sterilizing zone 39. In this fashion, 150 ml of aqueous hydrogen peroxide is introduced into the HEPA filter assemblies 35–37 and 80 ml of aqueous hydrogen peroxide is introduced into the lidstock sterilizing zone 39 through the nozzle 89 over about 15 min. During this step, the manifold temperature is maintained at about 44° C. and the cabinet temperature remains about 31° C.

With the valves 61 and 66 open and the valve 65 closed, 350 ml of aqueous hydrogen peroxide is introduced into the cabinet 11 through the nozzle 71 over a period of about 35 min. This final step of hydrogen peroxide injection provides a thorough wetting of all exposed surfaces within the aseptic zone 30 of the cabinet 11. The hydrogen peroxide laden air from the manifold 57 at about 44° C. condenses into a fog upon entry into the cabinet 11 which is at a temperature of about 31° C. This hydrogen peroxide fog provides a wetting of all exposed surfaces within the aseptic zone 30 of the cabinet 11 with a bactericidal concentration of hydrogen peroxide.

Sterilization of the interior of the cabinet 11 is completed by warming the air temperature within the cabinet 11 to enhance the sterilizing action of the hydrogen peroxide and to dry the sterilized surfaces. Thus, the temperature of the heat exchanger 51 is raised to increase the temperature of air in the hot air manifold 57 to about 148° C. This heating requires about 10 min. and is performed with all valves 61, 65 and 66 being closed. Upon reaching the target temperature, the hot air flow is maintained through the nozzles 19 until the temperature in the cabinet 11 reaches 44° C. The valves 61 and 66 are then opened to direct the hot air into the main portion of the cabinet 11 through the nozzles 19 and the conduit 68. After 20 min., the valve 66 is closed and the valve 65 is opened to direct the hot air flow into the HEPA filter assemblies 35–37 which attain a temperature of about 38° C. After a further 10 min., the valves 61 and 65 are closed, and the hot air from the manifold 57 is directed only through the nozzles 19 for 15 min. to provide a final drying of the cabinet interior and to reduce residual hydrogen peroxide levels to 0.5 ppm. It is preferred at this step to raise the temperature of the sterilizing wheel 91 to about 235° C. Activation of the blower 32 and establishment of the positive pressure zones P1, P2 and P3 in the cabinet 11 renders the machine 10 ready to commence a production run.

While the invention has been described in relation to the sterilization of the cabinet of the specific machine 10 described, the skilled person will appreciate that the invention has general application for the sterilization of a wide variety of machines. Accordingly, the scope of the invention is particularly defined by the following claims.

We claim:

1. A method for sterilizing internal surfaces of a cabinet enclosing an edible liquid packaging machine, comprising the steps of:

(1) providing a packaging machine enclosed within a cabinet, wherein the machine has a container sterilizing station, a product filling station, a container sealing station having a lidstock sterilizing zone with a lidstock sterilizing heater wheel, and an endless conveyor for receiving containers and transporting the containers to the container sterilizing station, product filling station, container sealing station, and then ejecting the filled and sealed containers from the machine, and wherein the machine is equipped with a positive pressure airflow through it, whereby the air is passed through an HEPA filter prior to its entry into the stations within the machine cabinet, and the machine having means for heating air prior to its entry into the machine cabinet;

(2) maintaining the cabinet at an air temperature of 28°–32° C., and injecting a fine spray of aqueous hydrogen peroxide into air flowing into the cabinet, whereby the inflowing air is heated to 40°–48° C., and directing the inflowing hydrogen peroxide laden air sequentially into the container sterilizing station, the container sealing station where a spray of aqueous hydrogen peroxide is also directed against the sterilizing heater wheel which is at 125°–150° C., and the container filling station, so that a fog of condensed aqueous hydrogen peroxide is provided in the stations for sufficient periods to effect complete contact of all exposed surfaces with a bactericidal concentration of hydrogen peroxide; and (3) upon termination of the injection of the fine spray of aqueous hydrogen peroxide, completing sterilization by heating dry inflowing air so that the internal cabinet temperature is raised to 41°–47° C. and the temperature of the HEPA filters is raised to 36°–40° C., and maintaining the temperatures and air flows for a sufficient time to effect sterilization and drying of all exposed surfaces of the container sterilizing, filling and sealing stations, thereby providing an aseptic zone for the packaging of an edible liquid.

2. A method as claimed in claim 1, wherein the cabinet air temperature for the first step is about 30° C. and the inflowing hydrogen peroxide laden air is heated to about 44° C.

3. A method as claimed in claim 1, wherein the fine spray of aqueous hydrogen peroxide contains 33% by weight hydrogen peroxide.

4. A method as claimed in claim 1, wherein the hydrogen peroxide laden air is initially caused to flow into the container sterilizing station for about 20 minutes.

5. A method as claimed in claim 1, wherein the hydrogen peroxide laden air is secondly caused to flow through all HEPA filters and then primarily into the container filling and sealing stations for about 15 minutes.

6. A method as claimed in claim 1 wherein the hydrogen peroxide laden air is thirdly caused to flow into a lower portion of the cabinet for about 35 minutes.

7. A method as claimed in claim 1, wherein the internal cabinet temperature in the second step is raised to about 44° C. and the air temperature in the HEPA filters is raised to about 38° C., and the heated air flows through the stations and HEPA filters are maintained for about 30 minutes.

* * * * *